US005286451A

United States Patent [19]
De Silva et al.

[11] Patent Number: 5,286,451
[45] Date of Patent: Feb. 15, 1994

[54] APPARATUS FOR CONTROLLED DELIVERY OF PARTICULATE MATERIAL

[75] Inventors: K. Nimalasiri De Silva; Roger Guevremont, both of Ottawa, Canada

[73] Assignee: Her Majesty the Queen in right of Canada, as represented by the Minister of Energy Mines and Resources, Ottawa, Canada

[21] Appl. No.: 64,366

[22] Filed: May 21, 1993

Related U.S. Application Data

[63] Continuation-in-part of Ser. No. 793,150, Nov. 18, 1991, abandoned.

[30] Foreign Application Priority Data

Nov. 23, 1990 [CA] Canada ................................ 2030588

[51] Int. Cl.[5] ....................... G01N 1/00; G01N 21/00; B01L 3/02; B65G 53/04

[52] U.S. Cl. .................................... 422/68.1; 422/81; 422/100; 73/864.81; 356/36; 406/93; 406/134

[58] Field of Search ........................ 422/68.1, 81, 100; 436/180; 73/864.11, 864.12, 864.13, 864.35, 864.81, 864.82, 864.83, 864.85; 34/10, 57 A, 57 R; 406/93, 94, 134, 146; 356/36

[56] References Cited

U.S. PATENT DOCUMENTS

| | | | |
|---|---|---|---|
| 2,716,042 | 8/1955 | Sylvander et al. | 302/42 |
| 3,447,381 | 6/1969 | Langtry et al. | 73/864.43 |
| 4,528,158 | 7/1985 | Gilles et al. | 422/63 |
| 4,590,165 | 5/1986 | Gilles et al. | 436/49 |
| 4,693,984 | 9/1987 | Minton et al. | 436/180 |
| 4,836,039 | 6/1989 | de Silva et al. | 73/864.81 |
| 4,859,121 | 8/1989 | Deysson et al. | 406/114 |
| 4,962,044 | 10/1990 | Knesel, Jr. et al. | 436/177 |
| 5,080,868 | 1/1992 | Elgas | 422/99 |

*Primary Examiner*—Robert J. Warden
*Assistant Examiner*—Christopher Y. Kim
*Attorney, Agent, or Firm*—Ronald G. Bitner

[57] ABSTRACT

An apparatus that provides controlled volumetric delivery of particulate material, particularly for delivery of a particulate sample for analysis. The apparatus includes a sample receiving tubular member that is vibrated or rotated relative to the sample container to agitate and fluidize a surface portion of the sample placed in an elongated container. A transporting gas carries the fluidized sample from the container through the tubular member. Sample delivery rate is controlled by a traversing mechanism that gradually inserts the moving tubular member into the upper fluidized portion of the sample. The apparatus allows total delivery of a known mass of a particulate sample at a predetermined delivery rate.

8 Claims, 2 Drawing Sheets

APPARATUS FOR CONTROLLED DELIVERY OF PARTICULATE MATERIAL

CROSS-REFERENCES TO RELATED APPLICATIONS

This is a continuation-in-part of U.S. patent application Ser. No. 07/793,150, filed Nov. 18, 1991, now abandoned.

FIELD OF THE INVENTION

This invention relates to a method and apparatus for controlled delivery of a particulate material and particularly for controlled volumetric delivery of a particulate sample for analysis.

BACKGROUND OF THE INVENTION

With the advent of high temperature excitation sources for analysis by optical atomic emission spectrometric methods, for example, Inductively Coupled Plasma Atomic Emission Spectrometry (ICP-AES), there has been a growing interest in the direct analysis of solids. This approach would bypass the tedious, time consuming and error-prone sample dissolution step involved in conventional analytical systems. However, the development of a practical method to introduce solids in a manner suitable for analytical purposes has been impeded by several major technological problems. The sample must be introduced uniformly so that the variations of the plasma characteristics are minimal. It is desirable to have a uniform sample delivery to satisfy the requirements of data acquisition techniques incorporated with most of the commercially available spectrometers. A controlled delivery of the sample is important to avoid overloading of the atomization source. It would be desirable to introduce a known amount of material within a desired time period. For a representative analysis the system should be able to introduce particles of a wide range of sizes and matrices without segregation according to size or density. Also, most systems require that the sample be transported in an inert gas.

There are several possible approaches to analyze solid materials without acid digestion, dissolution or other chemical processing to yield a liquid sample. Methods based on solid/liquid slurry nebulization, electrothermal vaporization, laser ablation, direct sample insertion have been proposed for analysis of solids. Methods based on the introduction of powders by the formation of a fluidized beds and aerosols has also been proposed to meet some of the analytical requirements.

A limitation of most of the systems previously described is that the analytical signals resulting from the introduction of the solid sample is transient; the mass of solid and the time duration of sample delivery is poorly controlled, or not controlled at all (e.g. laser ablation).

In U.S. Pat. No. 4,836,039 the present inventors have disclosed a method to generate a substantially uniform flow of particles by making use of a combination of mechanical agitation of the container and a flow of a gas for the generation of a fluidized bed.

However, none of the present systems provide all the features desired for solid sample delivery. Specifically, it would be desirable to be able to deliver a known mass of material within a known period of time, and to provide a constant feeding rate from the beginning to end of the sampling period. Furthermore, it would be desirable to be able to provide controlled delivery by electronic means under computer control to obtain a predetermined particulate material delivery rate, predetermined sampling intervals, etc.

SUMMARY OF THE INVENTION

An object of the present invention is to provide controlled volumetric delivery of particulate material.

Another object is to provide a system that facilitates delivery of particulate material at a predetermined constant volumetric rate.

Another object is to provide a system that facilitates delivery of particulate material at a substantially constant volumetric rate independent of other operating parameters such as gas pressure or gas flow rates.

Another object is to provide a system that facilitates the use of removable particulate material containers for sample changing.

Yet another object is to provide a system that facilitates total consumption of a known mass the particulate material from a particulate material container.

The present invention provides an apparatus for controlled volumetric delivery of particulate material, comprising; an elongated container having an opening for receiving particulate material to be delivered; container supporting means for receiving the container; a tubular member having a particulate material receiving inlet for insertion into the container, and an outlet; tubular member supporting means interconnected with and positioned relative to the container supporting means to allow insertion of the tubular member into the container; linear traversing means operatively interconnecting the tubular member supporting means with said container supporting means for traversing the tubular member relative to the container along a common longitudinal axis and towards the surface of the particulate material in the container at a predetermined rate selected to obtain the desired volumetric delivery rate of the particulate material; agitating means operatively associated with the tubular member and container supporting means for effecting agitating motion of the material receiving inlet of the tubular member relative to the container for agitating and fluidizing a surface portion of the particulate material within the container while the container is traversed relative to the tubular member; an enclosure surrounding the opening of the container for enclosing a region including the opening of the container and the particulate material receiving inlet of the tubular member; enclosure outlet means defining a passageway for the outlet of the tubular member allowing egress of fluidized material from the tubular member; and inlet means communicating with the enclosure for receiving a transporting gas for transporting particulate material from the fluidized surface within the container.

DESCRIPTION OF THE PREFERRED EMBODIMENTS

Figure 1:
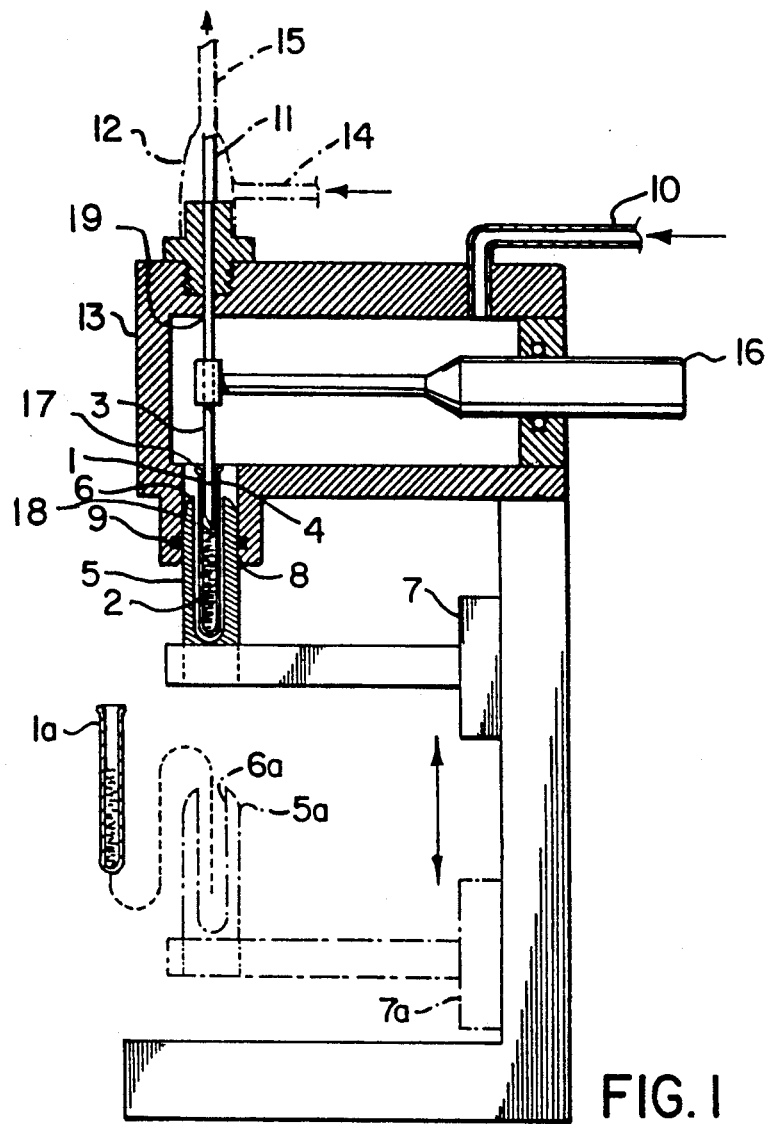
FIG. 1 is a schematic representation of one embodiment of the present invention.
Figure 2:
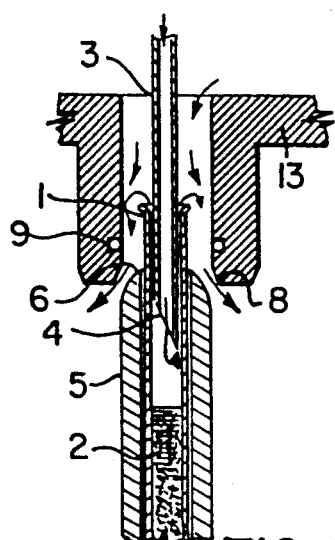
FIG. 2 shows details of a portion of the apparatus of FIG. 1 in preparation for, and prior to, particulate material delivery.
Figure 3:
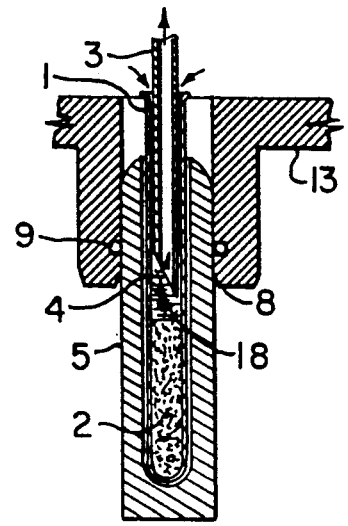
FIG. 3 shows details of a portion of the apparatus of FIG. 1 in operation for particulate material delivery.

With reference to FIGS. 1 to 3, the present invention comprises an elongated container 1 having an opening 17 for receiving particulate material 2 to be delivered, a tubular delivery member 3 for insertion into the container 1, and vibrating or oscillating means 16 for effecting oscillatory motion of the receiving inlet 4 of the tubular member 3 relative to the sample surface 18 for agitating and fluidizing a surface portion of the particulate material in the container 1.

The container 1 will preferably be removably supported by a suitable supporting member 5 shown as including a container receiving recess 6. The container supporting member 5 is shown to be movable vertically between the positions 5a and 5 by suitable traversing means 7. In the position (5), as shown in FIG. 1, the supporting member 5 is in sealing engagement with the opening 8 of the enclosure 13 with the use of a suitable seal 9. For delivery, as will be described, the traversing means 7 is adapted to move the supporting member 5 further upward at a predetermined rate, from the position (5) shown, to allow the receiving inlet 4 to reach the bottom of the container 1. The traversing means 7, in a lower position 7a, allows removal of a container for sample changing.

The traversing means 7, for the purpose of particulate material delivery, is selected to provide relative linear motion between the particulate material receiving inlet and particulate material at a predetermined rate. The traversing means should provide relative motion in a positive and quantifiable manner so that motion is independent of other uncontrolled parameters, such as gas pressure, physical properties of the particulate material, friction, etc. Suitable traversing means may include a mechanical mechanism or an electrical device such as a stepper motor.

The enclosure 13 includes inlet 10 for supplying a transporting gas for transporting the portion of the particulate material agitated and fluidized by the agitating tubular member 3 from the container. The fluidized sample is transported from the enclosure 13 through the outlet of the tubular member 3 which is sealingly positioned within the outlet passageway 19.

The preferred application of the present invention is for delivery of a particulate sample to an analyzing device (not shown). For this purpose the outlet 11 of the tubular member 3 may communicate with a flow combining portion 12 where flow from outlet 11, which includes entrained particles from container 1, is combined with a carrier gas supplied at inlet 14.

To begin operation the container 1a is filled with the particulate sample, and the tube is fitted into the recess 6a of the container supporting member 5a. The traversing means 7 is moved from position 7a to 7 to bring the sample toward the tip 4 of the tubular member 3. The directions of the gas flows before the container supporting member 5 reaches the seal 9 are shown in FIG. 2. A portion of the gas flow entering inlet 14 exits the flow combining portion 12 through the outlet 11 of tubular member 3 and then through the unfilled portion of the container 1 to the atmosphere. This ensures that any remaining air inside the container will be purged before the container supporting member 5 reaches the seal 9.

The gas flow entering inlet 10 escapes through the opening 8 in enclosure 13 and prevents contamination of enclosure 13 with air.

The relative positioning of the inlet end 4 of the tubular member 3, seal 9, the upper end of the container supporting member 5, and the position of the sample is arranged such that the tubular member 3 does not reach the sample 2 until the container supporting member 5 is in sealing engagement with the opening 8 of enclosure 13 as shown in FIG. 3.

Due to the forces generated by the transporting gas, it may be necessary to provide means for securing the container 1 within the receiving recess 6 of the supporting member 5.

In operation, particulate material delivery is initiated by relative placement of the inlet end 4 of the tubular member 3 into proximity with the surface of the particulate material. In the embodiment shown in FIG. 1, the traversing means 7 is used to move the supporting member 5 and particulate material container 1 upward into contact with the inlet end 4 of the tubular member 3. The particulate material at the surface of the sample is fluidized by the motion of the tubular member 3, and carried to the sample analyzing device through the tubular member 3 due to high linear velocity of the gas as shown in FIG. 3. The agitation of the sample provides uniform erosion of particles on the surface and reduces abrupt changes in entrainment of the particulate material through the tubular member 3. As delivery proceeds, only the surface portion of the sample is fluidized, and therefore segregation of particles due to variations in size and mass is avoided. However, when beginning and ending delivery it is possible that some segregation of particles can occur.

The delivery rate of the particulate material is controlled by the rate that the inlet end 4 of the tubular member is inserted into the downwardly eroding surface of the particulate material 2 by traversing means 7. Delivery of the particulate material can readily be started and stopped by starting and stopping the traversing means 7, for example, with suitable electrical control means. If necessary the inlet end 4 of the tubular member 3 can be withdrawn from the surface of particulate sample 2 in order to ensure complete stopping of the flow of particulate material.

It should be noted that particulate material delivery can be stopped and started at any time without any alteration to the gas flows entering at inlets 10 or 14. In this way the gas flow rate to the analyzing device does not alter during changes in particulate material delivery rate. Furthermore, the flow rates of gas, and the gas pressure within chamber 12 and 13 can be allowed to stabilize before any particulate material is carried to the analyzing device. The above is important for application of the present invention to chemical analysis of samples using analyzing devices based on plasmas or flames.

The rate of transporting gas flow supplied to inlet 10 is selected to provide efficient transport of the particulate material through the tubular member, and in particular, must be sufficient to provide removal of all the particulate material that is fluidized in the container. A carrier gas may be supplied to flow combining portion 12 at inlet 14 to provide a make-up gas to match the requirement of the analyzing device.

The flow combining portion 12 will preferably define an annulus around the outlet 11 of the tubular member such that gas flow to the analyzing device (not shown)

via conduits 15 will exit in the form of a sheath or spiral flow to maintain the sample particles at the centre of the gas stream. This will reduce the deposition of particles along the walls which can cause carry over from one sample to the other. The net gas flow entering to the analyzing device will be the sum of the two flows provided at inlets 10 and 14.

It should be noted that by progressively agitating and fluidizing only the surface portion of the particulate material sample 2, the delivery rate is controlled by the traversing means 7, and the delivery rate of particulate material is essentially independent of the gas flow rates or gas pressure supplied at inlets 10 and 14, or physical properties of the particulate material. The traversing means controls the point where agitation occurs and thereby allows positive control of delivery rate by direct mechanical control of the traversing rate. Particulate material delivery rate is determined by the linear motion of the tubular member 3 inlet relative to the particulate material container 1, which is controlled by the traversing means 7. Specifically, the volumetric delivery rate is the product of the cross-sectional area times the linear velocity of the tubular member 3 relative to the particulate material container 1.

Preferably the cross-sectional area will be uniform so that delivery rate is dependent only on the linear motion of the tubular member relative to the particulate material container 1. For most applications it will be desirable that delivery rate be constant which is achieved by arranging that the linear velocity of the tubular member relative to the particulate material container 1 is constant. Hence, by moving the particulate material container 1 upwardly at a constant rate until its bottom reaches the inlet tip 4, provides that the total sample material is introduced at essentially the same feeding rate throughout. The constant relative velocity also facilitates achieving steady state operation.

Total consumption of the sample simplifies quantitative analysis since the amount of unused sample need not be measured. Also total consumption of the sample reduces the tendency of sample segregation wherein particles are preferentially retained in the container due to difference of size, shape, density, etc. To achieve total consumption of a sample, the components will be arranged to allow the inlet tip 4 to reach the bottom of the container 1, which will be provided with a suitable geometry to facilitate egress of all material.

Figures 4, 5:
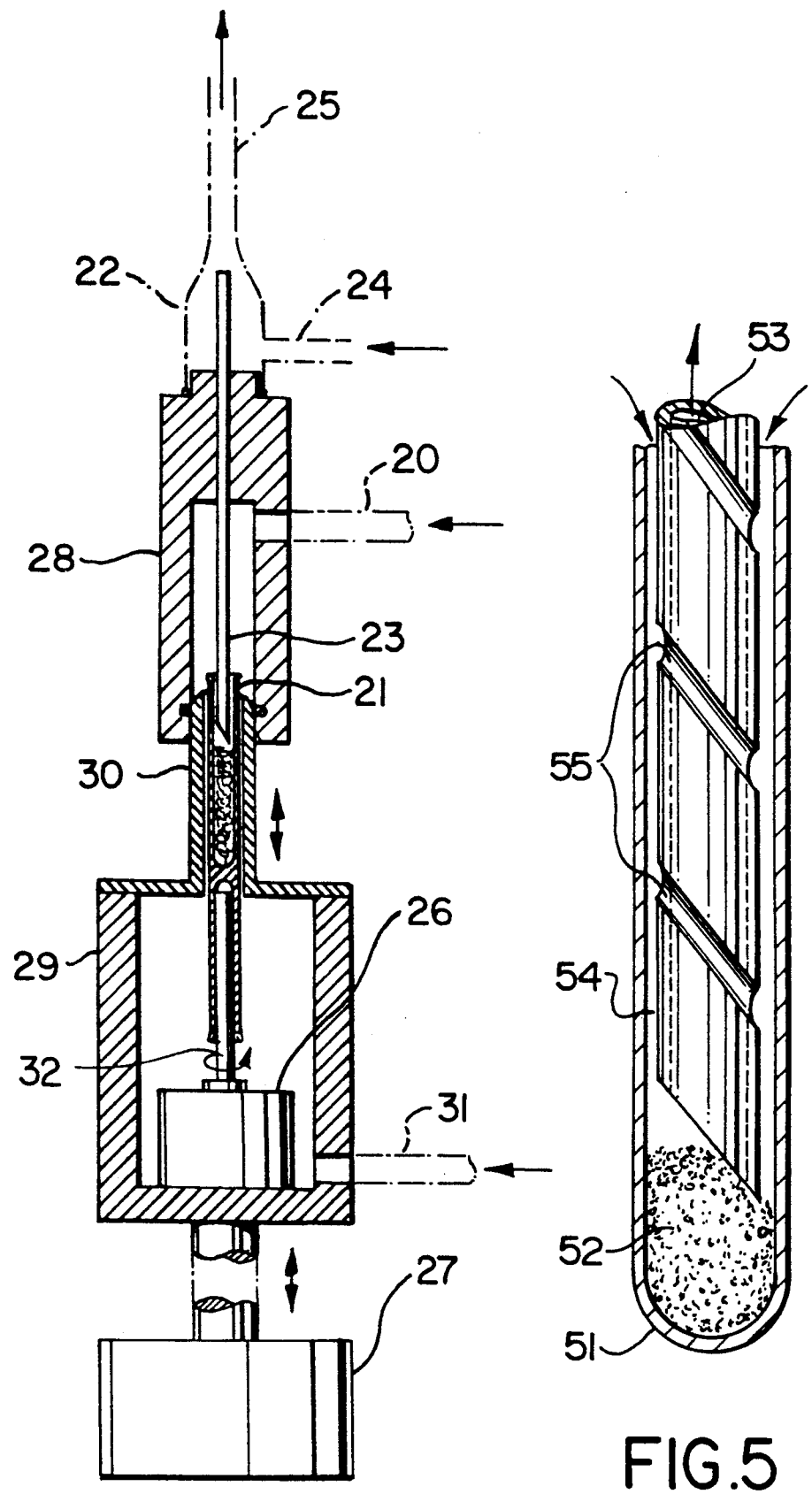
FIG. 4 is a schematic representation of another embodiment of the present invention.
FIG. 5 shows details of one specific embodiment of the tubular member shown within a particulate material container.

Means for avoiding the retention of small particles on the walls of the container is shown in FIG. 5. FIG. 5 shows details of one embodiment of the tubular member 53 in combination with a container 51 containing a particulate sample 52. As shown, the outside diameter of the tubular member 53 is nearly equal to the inner diameter of the container 51. This relationship defines a small intervening passageway 54 for the transporting gas which provides that the transporting gas passes between the outer walls of the tubular member 53 and the inner walls of the container 51 with high velocity. The high velocity transporting gas serves to carry residual particles of sample from the walls of the container 51, facilitating total consumption of the sample. In FIG. 5, the tubular member 53 is shown to have a spiral groove 55 on the outer surface which defines an additional passageway for the transporting gas which ensures that all portions of the inner walls of the container will be swept with the high velocity transporting gas as the tubular member 53 is traversed relative to the container 51. The grooves overcome the problem that arises if the intervening space 54 is too small to provide adequate flow of transporting gas, or when the tubular member is off center or contacting the walls of the container, which would otherwise prevent all particles from being removed from the walls of the container 51.

An alternate approach that provides sweeping of the sides of the container with transporting gas is the use of a tubular member with flattened or non-circular sides and rotating the container as with the apparatus shown in FIG. 4.

Preferably the ratio of length of the column of sample 52, defined by the inner dimensions of container 51, relative to the diameter will be high. A high traversing rate of the tubular member relative to container, for a given sample delivery rate, together with having a tubular member 53 diameter that is only slightly smaller than the container 51 reduces the likelihood of abrupt entrainment of portions of the sample as the tubular member 53 is traversed and hence provides high uniformity of sample delivery.

Various means may be used for fluidizing the surface layer of sample 2 as appearing in FIGS. 1 to 3. In an embodiment such as illustrated in FIG. 1, suitable means for agitating the sample can include an ultrasonic or electromagnetic transducer 16 that vibrates the particulate material receiving inlet 4 of the tubular member 3. Fluidization can be effected by various agitation means that provides relative motion between the inlet 4 of the tubular member 3 and container 1. For example, either, or both, of the tubular member or the container can be vibrated, rotated, oscillated, or otherwise moved relative to the other. The amount of agitation required for fluidization of the surface of the sample will vary depending on the physical properties, such as size, density, and/or electrostatic properties of the sample particles. For example, for certain materials the sample may be fluidized sufficiently by the flow of transporting gas alone. For material having dense or large particles additional agitating means such as shown in FIG. 1 may be required.

For certain sample materials, for example those which do not flow readily, it may be desirable to use a tip 4 that is elliptical or flattened, or one that is provided with an inner projections, or other suitable means, that prevents the formation of an inner pillar or core of the sample material as the tubular member 3 is traversed into the sample. This avoids irregularities in the mass transport rate of the particulate material carried with the transporting gas.

FIG. 4 shows an embodiment for fluidizing the particulate material by rotating the container 21 which is removably attached by retaining means 32 to rotatable means 26.

As in the embodiment of FIGS. 1 to 3, removability of container facilitates exchange of samples. In addition, since a new sample is in a new container, carry-over from a previous sample is minimized.

Unlike the embodiment of FIGS. 1 to 3 the tubular member 23 is stationary while the rotation of the container 21 provides the relative motion between the container 21 and tubular member 23.

In FIG. 4 the container supporting means includes the container retaining member 32, disposed on rotating means 26, and the sleeve portion 30 attached to the enclosure 29.

In a manner similar to that of the embodiment of FIGS. 1 to 3, a transporting gas can be supplied at inlet 20 for transporting material from the container 21. A carrier gas may be supplied at inlet 24 of combining chamber 22 to further carry the material to an analyzing device (not shown) via conduit 25. Alternatively, the transporting gas can be supplied via inlet 31 in enclosure 29 which communicates with enclosure 28 via the sleeve portion 30.

The lower enclosure 29 may be provided with an inlet 31 for receiving a small quantity of inert gas to avoid contamination of enclosure 29 with air while sleeve portion 30 is disengaged from opening 33 of enclosure 28. At other times the inlet 31 can be closed, or, as indicated above may also be used to provide the transporting gas for transporting the fluidized sample from the container 21.

As in the embodiment of FIG. 1, the delivery rate of the particulate material is a function of the rate that the inlet end of the tubular member 23 is inserted into the particulate material by traversing means 27.

It should be noted that in both embodiments described above, the same traversing means is used to provide the two functions of providing the relative motion between the inlet end of the tubular member and the particulate material, and also for moving the container supporting means and enclosure opening means relative to one another for sealing and providing access means for sample changing. It will be understood that these two functions could be provided by separate means. For example, in an alternative arrangement the traversing means 27 shown in FIG. 4 could be located inside the enclosure 29, in which case other separate traversing means would be used to engage and disengage member 30 from enclosure 28. Also, in another embodiment of the invention the traversing means and fluidizing means could be provided by the same device.

Following are details of an embodiment of the present invention found to be suitable for ICP spectrometry. The desired flow rate of particulate material for the proper operation of the plasma is about 10 mg/min. The sample weight will preferably be in the range of 10 mg to 100, typically 30 mg. The particle size of the sample should be 50 μm or less, typically about 20 μm. A suitable tubular member, in the form of a capillary, has an outside diameter of 0.7 mm and inside diameter of 0.4 mm. A suitable container has an inside diameter of 0.75 mm and length of 5 cm to provide a traversing distance of 3 cm. A suitable traversing rate is about 1 cm/min.

It will be understood that the present invention may be utilized in various applications other than that described above which require controlled delivery of particulate material.

What is claimed is:

1. An apparatus for controlled volumetric delivery of particulate material, comprising:
   an elongated container having an opening for receiving particulate material to be delivered;
   container supporting means for receiving the container;
   a tubular member having a particulate material receiving inlet for insertion into the container, and an outlet;
   tubular member supporting means interconnected with and positioned relative to the container supporting means to allow insertion of the tubular member into the container;
   linear traversing means operatively interconnecting the tubular member supporting means with said container supporting means for traversing the tubular member relative to the container along a common longitudinal axis and towards the surface of the particulate material in the container at a predetermined rate selected to obtain the desired volumetric delivery rate of the particulate material;
   tubular member agitating means operatively associated with the tubular member and container supporting means for effecting agitating motion of the material receiving inlet of the tubular member relative to the container for agitating and fluidizing a surface portion of the particulate material within the container while the container is traversed relative to the tubular member;
   an enclosure surrounding the opening of the container for enclosing a region including the opening of the container and the particulate material receiving inlet of the tubular member;
   enclosure outlet means defining a passageway for the outlet of the tubular member allowing egress of particulate material from the tubular member; and
   inlet means communicating with the enclosure for receiving a transporting gas for transporting particulate material from the fluidized surface portion within the container;
   wherein the agitating means in combination with the movement of the linear traversing means towards the surface of the particulate material in the container fluidizes only the surface portion of the particulate material and the transport gas transports the fluidized particulate material out of the container through the tubular member.

2. The apparatus of claim 1, wherein the enclosure comprises opening means for providing access for container removal.

3. The apparatus of claim 2, wherein said container supporting means and enclosure opening means include mating separable sealing surfaces; and further comprising means for moving the container supporting means relative to the enclosure and into sealing engagement with the enclosure.

4. The apparatus of claim 1, wherein said container has a substantially uniform cross-sectional area.

5. The apparatus of claim 1, wherein said container supporting means comprises releasable retaining means for the container.

6. The apparatus of claim 1, further comprising a flow combining portion connected with the outlet of the tubular member, said combining portion having an inlet for a carrier gas, and an outlet for connection with an analyzing device.

7. The apparatus of claim 1, wherein the outer surface of the tubular member is non-circular for defining a passageway between the outer surface of the tubular member and the inner surface of the container for the transporting gas for sweeping residual particles of the particulate material from the walls of the container as the container is traversed and rotated relative to the tubular member.

8. The apparatus of claim 1, wherein the outside surface of the tubular member includes a spiral groove for defining a passageway for the transporting gas for sweeping residual particles of the particulate material from the walls of the container as the container is traversed relative to the tubular member.

* * * * *